(12) United States Patent
Carpenter et al.

(10) Patent No.: US 7,144,421 B2
(45) Date of Patent: Dec. 5, 2006

(54) ENDOVASCULAR PROSTHESIS, SYSTEM AND METHOD

(76) Inventors: Judith T. Carpenter, 851 Box Hill La., Radnor, PA (US) 19087; Jeffrey P. Carpenter, 851 Box Hill La., Radnor, PA (US) 19087

( * ) Notice: Subject to any disclaimer, the term of this patent is extended or adjusted under 35 U.S.C. 154(b) by 0 days.

(21) Appl. No.: 10/702,864

(22) Filed: Nov. 6, 2003

(65) Prior Publication Data
US 2005/0102018 A1 May 12, 2005

(51) Int. Cl.
*A61F 2/06* (2006.01)
(52) U.S. Cl. .................... 623/1.31; 623/1.35
(58) Field of Classification Search .............. 623/1.27, 623/1.3, 1.31, 1.35, 1.25
See application file for complete search history.

(56) References Cited

U.S. PATENT DOCUMENTS

| | | | | |
|---|---|---|---|---|
| 5,476,506 A | * | 12/1995 | Lunn .......................... | 623/1.28 |
| 6,428,565 B1 | * | 8/2002 | Wisselink ................... | 623/1.11 |
| 6,478,817 B1 | * | 11/2002 | Schmitt et al. ............. | 623/1.35 |
| 6,770,090 B1 | * | 8/2004 | Gantt et al. ................ | 623/1.35 |
| 6,932,837 B1 | * | 8/2005 | Amplatz et al. ............ | 623/1.15 |
| 2001/0014794 A1 | | 8/2001 | Moll et al. .................. | 604/289 |
| 2002/0198585 A1 | | 12/2002 | Wisselink ................... | 623/1.11 |
| 2003/0120333 A1 | | 6/2003 | Ouriel et al. ............... | 623/1.14 |
| 2004/0117003 A1 | * | 6/2004 | Ouriel et al. ............... | 623/1.35 |
| 2004/0193254 A1 | * | 9/2004 | Greenberg et al. ......... | 623/1.35 |

* cited by examiner

*Primary Examiner*—Corrine McDermott
*Assistant Examiner*—Thomas J. Sweet
(74) *Attorney, Agent, or Firm*—Michael F. Petock, Esq.; Petock & Petock, LLC (57) ABSTRACT

An endovascular prosthesis comprising a first end section, a second end section and a midsection. The midsection has a diameter less than the diameter of the first end section and the second end section. At least the first end section and the second end section have lateral support preferably in the form of a stent which may also act as anchoring. The reduced diameter midsection is provided with at least one side port which is adapted to be connected to a branch endograft to provide a connection between the side port and the native branch artery. The side ports are arranged to correspond with the native branch arteries and are provided with radiographic markers at their proximal and distal ends. The side ports with the radiographic markers provide an effective means of making the connection to the native branch by a branch endograft without having to align the side ports exactly to the branch arteries and without kinking of the side ports.

60 Claims, 5 Drawing Sheets

ENDOVASCULAR PROSTHESIS, SYSTEM AND METHOD

FIELD OF THE INVENTION

The present invention relates to an endovascular prosthesis, system and method. More particularly, the present invention relates to an endovascular prosthesis which provides improved connection between the endovascular prosthesis which may be positioned in a major artery, such as the aorta, and branch arteries. The present invention also relates to a system and method of endovascular prosthesis placement.

BACKGROUND OF THE INVENTION

Degenerative diseases of the arteries such as aneurysms and dissections often necessitate arterial replacement. Conventional open surgery for arterial replacement is associated with significant risk of death or disability and may be especially dangerous for the vascular patient who typically has significant pre-existing surgical risk factors.

Minimally invasive alternatives to open vascular surgery have been developed, chiefly employing endovascular means whereby arterial replacement is performed by placement of an endovascular prosthesis via a remote access point. Such endovascular prostheses are usually comprised of an impervious fabric through which blood flows, preventing contact with the diseased arterial wall. The fabric may be sealed to disease-free arterial wall above and below the diseased segment of artery to be bypassed. These endovascular prostheses have been successfully applied to repair disease of the thoracic and abdominal aorta and peripheral arteries, where tubular prostheses without branches may be employed. A limitation on the applicability of these prostheses has been their inability to repair branched arteries.

Examples of regions of the aorta commonly affected by arterial disease which include branches are the aortic arch, from which the innominate, carotid and subclavian arteries originate, and the proximal abdominal aorta, from which the visceral and renal arteries emerge as side branches. Although grafts have been designed with end branches to accommodate the iliac arteries, no commercially available device exists with side branches to accommodate the thoracic and abdominal aortic branches.

Recently, there have been some attempts at the design of branched prostheses. All of these have inherent problems which have been overcome by the present invention.

For example, U.S. Pat. No. 5,424,765—Tifenbrun et al. discloses a prosthesis with holes custom cut into the sides of the main tubular body prior to surgery based on radiographic measurements of individual patients. These holes must be precisely aligned with the side branch arteries to be replaced. This is often difficult or impossible in actual practice owing to the variability in individual patient anatomy and the difficulty of accomplishing this precise alignment in vivo. Additionally, blood may leak into the segment which is to be excluded by means of this fenestration, rather than flow exclusively into the intended branch vessel.

U.S. Pat. No. 6,428,565 B1—Wisselink discloses a device whereby side branch endografts may be inserted through holes formed in a tubular main body prosthesis. This approach has also been limited by the need for precise alignment of the side-holes with the native arterial branch origins. This is difficult to accomplish in vivo, again owing to the variability of anatomy of individual patients and difficulties in obtaining precise alignment of the prosthesis at the time of implantation. Small measurement errors may result in either longitudinal or circumferential misplacement of these side holes, and this may result in the kinking of the branch endografts as they attempt to reach the native branch vessel.

U.S. patent application No. US 2003/0120333 A1—Ouriel discloses a prosthesis which terminates in multiple end branches which may be connected to branch arteries. This design is limited by crowding of multiple branches within the native aorta which may lead to radiographic confusion in their identification and limit their ability to be manipulated within a confined space. In addition, the necessary use of multiple long sheets of small tubular conduits may be prone to thrombosis and graft failure. The multiple end branches may also be prone to kinking as the end branches interweave on their paths to the various end arteries. As each of the end branches is deployed each successive branch will be more difficult to maneuver in the crowded lumen of the aorta.

SUMMARY OF THE INVENTION

An advantage of the present invention is that it provides a reduced diameter midsection on which one or more side branches may be placed thereby allowing maneuvering of branch endografts to connect between side ports and native branches.

Another advantage of the present invention is that the side ports on the midsection may be positioned and aligned to facilitate easy placement of endografts through them into branch vessels.

Another advantage of the present invention is that the side ports allow for accurate branch endograft placement without kinking despite variations in location of native vessels.

Another advantage of the present invention is that the location of the side ports in the reduced diameter midsection of the prosthesis reduces the overall diameter of the device for easier insertion.

Another advantage of the present invention is that the prosthesis of the present invention is able to connect to commercially available thoracic, abdominal and branch endografts to allow repair of the entire aorta and its branches.

Another advantage of the present invention is that the prosthesis may be modified by variation in side port arrangement for use in the aortic arch, suprarenal or juxtarenal positions.

Another advantage of the present invention is that the geometric arrangement of the side port branches will allow for easy radiologic identification of the branches for guide wire insertion.

Briefly, in accordance with the present invention, an endovascular prosthesis comprises a first end section having a longitudinally extending central lumen and means for laterally supporting said first end section. A second end section is provided which has a longitudinally central lumen and means for laterally supporting the second end section. A midsection is formed between the first end section and the second end section and provided with a longitudinally extending central lumen in communication with said longitudinally extending central lumens of the first and second end sections. The midsection has a diameter less than the diameter of the first end section and less than the diameter of the second end section and the reduced diameter midsection is provided with at least one side port adapted to be connected to a branch endograft.

In a presently preferred embodiment, the reduced diameter midsection would have multiple side ports which are arranged to correspond to the approximate position of the native branch arteries. Each side port is provided with proximal and distal radiologic markers allowing easy radiological identification of the side ports for enhanced ability to implant branch endografts between the side port and the native branch artery.

In accordance with a presently preferred embodiment, the reduced diameter midsection would have tapers providing a smooth transition from the larger diameters of the first end section and the second end section.

In accordance with a preferred embodiment, the lateral support means of the first end section and the second end section may be stents mounted on the outer surface of the prosthesis. Further, in a presently preferred embodiment, the stents may be of a resilient material which would automatically expand into place upon being released from the delivery catheter.

The present invention also includes the endovascular prosthesis system and the method of implantation of the endovascular prosthesis.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
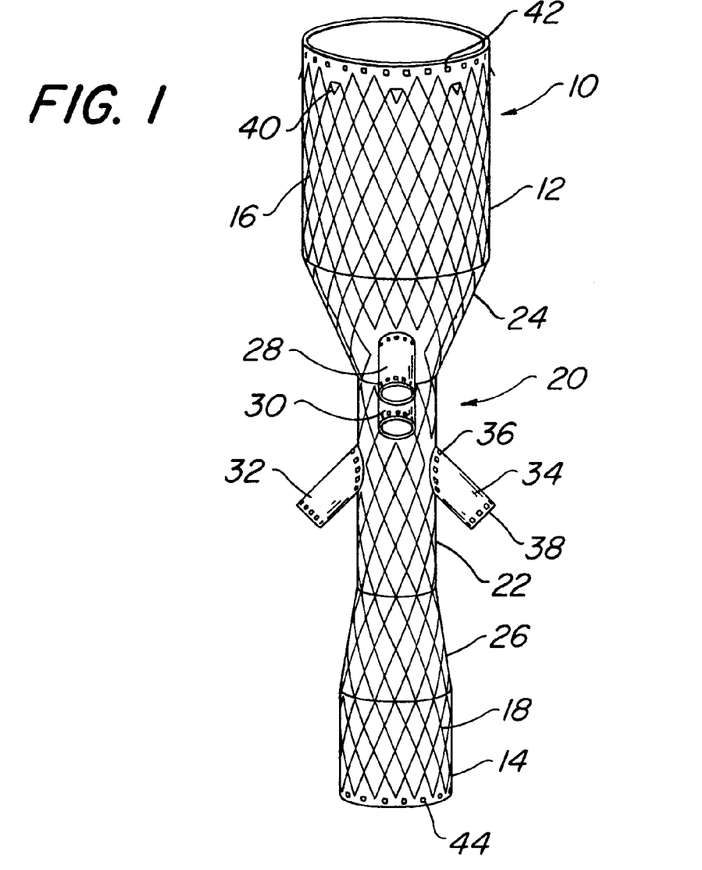
FIG. 1 is an elevation view of one embodiment of an endovascular prosthesis in accordance with the present invention.

Referring now to the drawings wherein like numerals indicate like elements, there is shown in FIG. 1 an endovascular prosthesis 10 in accordance with the present invention. Endovascular prosthesis 10 is provided with a first end section 12 and a second end section 14. Both first end section 12 and second end section 14 have a longitudinally extending central lumen and means 16 and 18, respectively, for laterally supporting first end section 12 and second end section 14, respectively. The means for laterally supporting the first end section 12 and second end section 14, as well as midsection 20 to be discussed, may be any suitable means for providing lateral support, but in a presently preferred embodiment, the lateral support means may be a resilient stent formed on the outer surface of endovascular prosthesis 10 as illustrated in FIG. 1 which may be compressed, but automatically expands upon release of the compressing force.

Midsection 20 is formed between first end section 12 and second end section 14 and is provided with a longitudinally extending central lumen in communication with the longitudinally extending central lumens of said first end section and said second end section. Midsection 20 is provided with a diameter which is less than the diameter of the first end section 12 and less than the diameter of the second end section 14. Typically, the diameter of first end section 12 would be larger than the diameter of second end section 14, but this is not necessarily the case.

Midsection 20 includes three portions, including a central reduced diameter portion 22, a tapered portion 24 extending from first end section 12 to central portion 22 and a second tapered portion 26 extending from second end section 14 to central portion 22. Tapered herein means any gradual decrease in the diameter of the portion, and not necessarily uniformly decreasing or straight line decreasing tapered as illustrated in FIG. 1 and the other figures. Midsection 20, including central portion 22 and tapered portions 24 and 26 are provided with lateral support means similar to that as discussed with respect to the first and second end sections 12 and 14.

Midsection 20 is provided with at least one side port which is adapted to be connected to a branch endograft to form communication between the central lumen of endovascular prosthesis 10 and a native branch artery. In a presently preferred embodiment of a juxtarenal endovascular prosthesis 10 as illustrated in FIG. 1, midsection 20 would be provided with four short side ports, namely side port 28 for connection to the celiac artery, side port 30 for connection to the superior mesenteric artery (SMA) and two renal side ports 32 and 34.

First end section 12 may be provided with radiologic markers 42 and second end section 14 may be provided with radiologic markers 44. Each of the side ports may be provided with radiologic markers at its proximal end and distal end. For example, side port 34 is provided with radiologic markers 36 at its proximal end and radiologic markers 38 at its distal end.

In a presently preferred embodiment of the present invention, endovascular prosthesis 10 may be anchored by the expansion of resilient stent 16 against native arterial wall or another endovascular prosthesis. However, various other anchoring means may be utilized including balloon expandable stents, hooks, barbs, quills, polymer, adhesive and any other suitable means. As illustrated, for example in FIG. 1, hooks 40 on first end section 12 may extend radially outwardly and in the direction of arterial flow.

The body of the prosthesis may be comprised of an impervious material such as polyester, polytetrafluoroethylene (PTFE) or other suitable materials. The material is longitudinally supported throughout by a supporting skeleton of metal, polymer, foam or other such supporting means.

Figure 7:
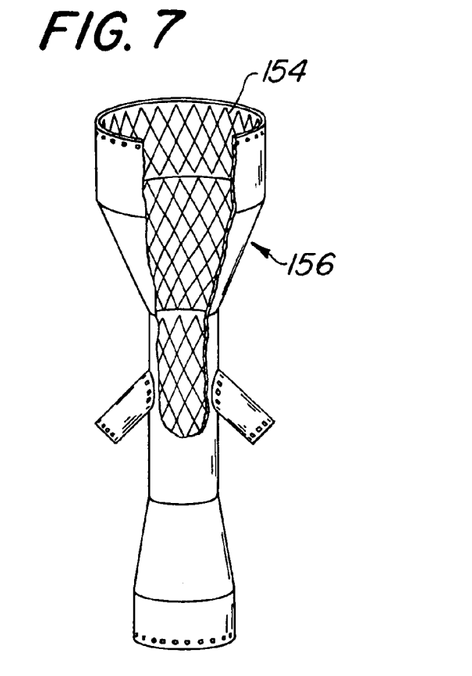
FIG. 7 is an elevation view, partially broken away, of another embodiment of an endovascular prosthesis in accordance with the present invention.
Figure 8:
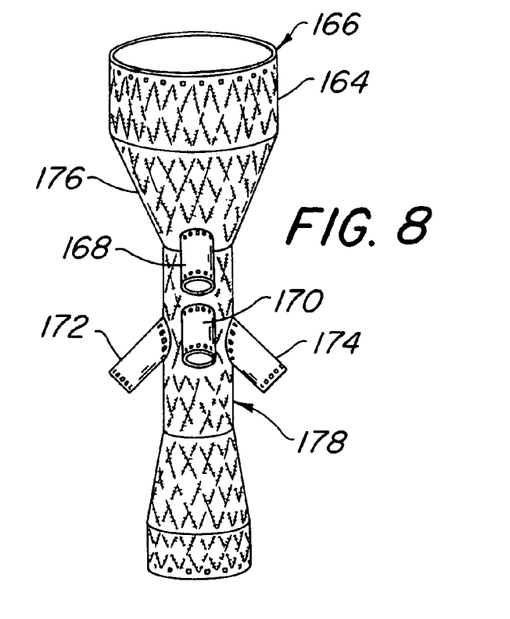
FIG. 8 is an elevation view of another embodiment of an endovascular prosthesis in accordance with the present invention.

Endovascular prosthesis 10 may be anchored at first end 12 to native arterial wall or to another endovascular prosthesis. Anchoring is preferably by means of a resilient stent formed on the outside of the impervious material thereby eliminating the possibility of a guide wire catching the stent wire, but the stent wire may be embedded between two layers of impervious material as shown in FIG. 8 or contained on the inner surface of the impervious material as illustrated in FIG. 7. The anchoring alternatively may be by means of stents, hooks, barbs, quills, polymer or other suitable anchoring means. The anchoring hooks or barbs may be pointed in the direction of arterial flow and radially outward from the prosthesis.

The first end section 12 or proximal end (proximal here meaning closer to the heart) may be of a diameter comparable to that of the vessel or endograft into which the first end is to be placed in such a way as to form an impervious seal with the vessel or endograft. The tubular prosthesis tapers beyond the first end section sealing zone to a smaller diameter midsection. The reduced diameter midsection allows the side port branches adequate room to emerge from the main tubular body. The second end section 14 or distal end of the tubular endovascular prosthesis is of a diameter comparable to that of the vessel or endograft to which it will be attached in such a way as to form an impervious seal with the vessel or endograft.

The endovascular prosthesis of the present invention may be constructed of various dimensions and would preferably be constructed of various dimensions to accommodate various anatomical variation. However, by way of example and illustration, and not by way of limitation, the approximate dimensions in millimeters of one embodiment may be:

| | |
|---|---|
| Diameter of first end section 12 | 34 mm |
| Diameter of central portion 22 of midsection 20 | 14 mm |
| Diameter of second end section 14 | 20 mm |
| Length of first end section 12 | 40 mm |
| Length of tapered portion 24 | 20 mm |
| Length of central portion 22 | 40 mm |
| Length of tapered portion 26 | 20 mm |
| Length of end section 14 | 20 mm |

A number of short hollow tubular side ports appropriate to the number of native arterial branches to be connected in the anatomical region being reconstructed are provided. The lumens of the side ports communicate directly with the lumen of the main body of the endovascular prosthesis and are attached to the main body in an impervious manner. The side ports emerge sequentially from the midsection of the tubular endovascular prosthesis at angles which are directed toward the origins of the native arterial vessels to which they are destined to supply blood flow. The side ports need not be in precise alignment with the native arteries since the narrow midsection allows room for maneuvering within the aortic lumen and the angled orientation of the side ports facilitates direction of a guide wire into the native vessels when manipulated through the prosthetic side port. All that is required is that a guide wire connection be established between the prosthetic side port and the native artery which it is to supply.

Figure 6:
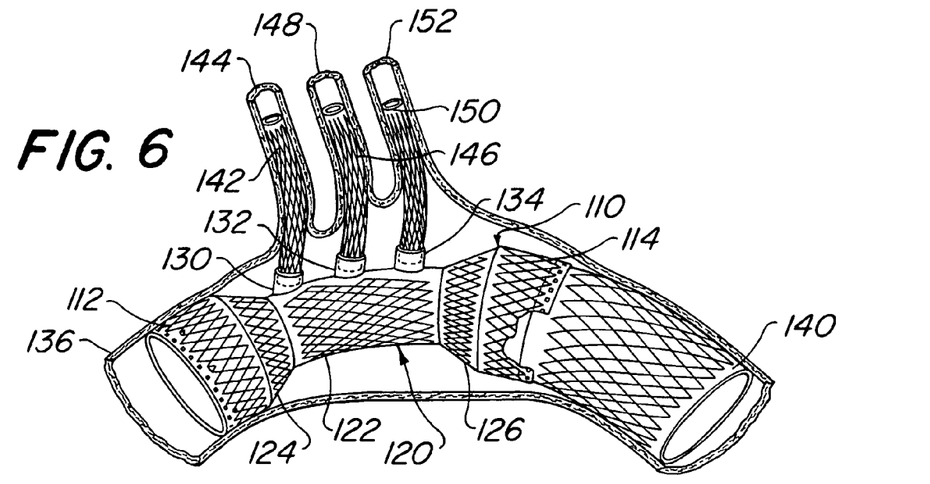
FIG. 6 is an elevation view, partially in cross section, of another embodiment of an endovascular prosthesis in accordance with the present invention implanted in the aortic arch, being attached proximally to the aortic arch wall and being attached distally to a thoracic endograft, with side ports being connected by branch endografts to the innominate, left carotid and left subclavian arteries.

The side ports are positioned along the length of the tubular midsection in a geometric arrangement which parallels that of the orientation of the native vessels they are intended to supply. For example, as illustrated in FIG. 1, celiac side port 28 originates proximal to SMA side port 30, which originates proximal to the renal side ports 32 and 34. The endovascular prosthesis of the present invention would have a different side port arrangement when used for aortic arch replacement, as illustrated in FIG. 6, to be discussed hereinafter.

The side ports may be comprised of an impervious material such as polyester, PTFE, or other suitable material. The side port material may be longitudinally supported by a skeleton of metal, polymer, foam or other supporting means. A ring support may be provided in the open distal end of each tubular side port and the open proximal end of the side port at the point of origin from the main body of the endovascular prosthesis, to ensure branch patency and to facilitate radiological visualization of the ends of the side port tube. Alternatively, radiologic markers may be provided as discrete elements.

Figure 2:
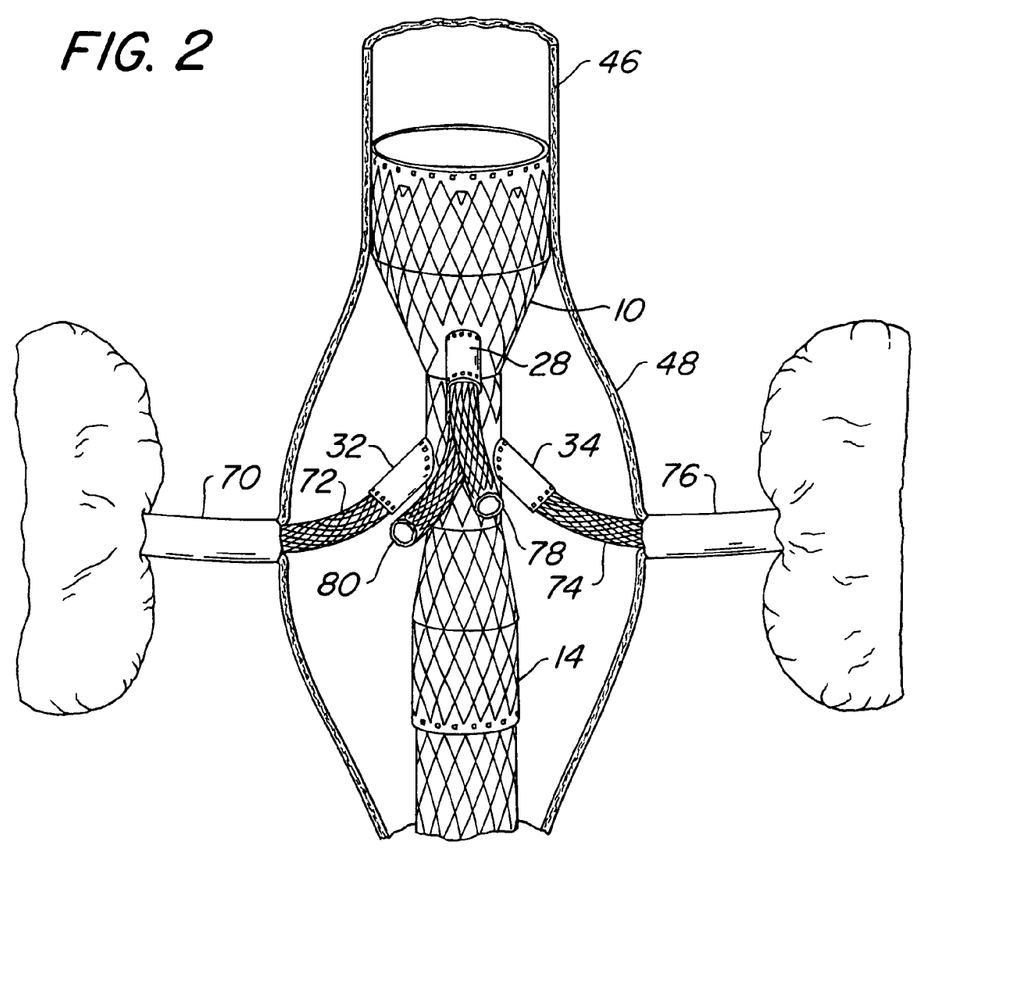
FIG. 2 is an elevation view, partially in cross section, of one embodiment of an endovascular prothesis in accordance with the present invention implanted juxtarenally in the aorta, being anchored proximally to the aortic wall and anchored distally to an infrarenal endograft.

Referring now to FIG. 2, there is shown an endovascular prosthesis 10 juxtarenally implanted in the aorta 46. Aorta 46 has an aneurysm 48. Endovascular prosthesis 10 may be delivered via a delivery catheter 50 illustrated in FIGS. 4 and 5.

Figure 4:
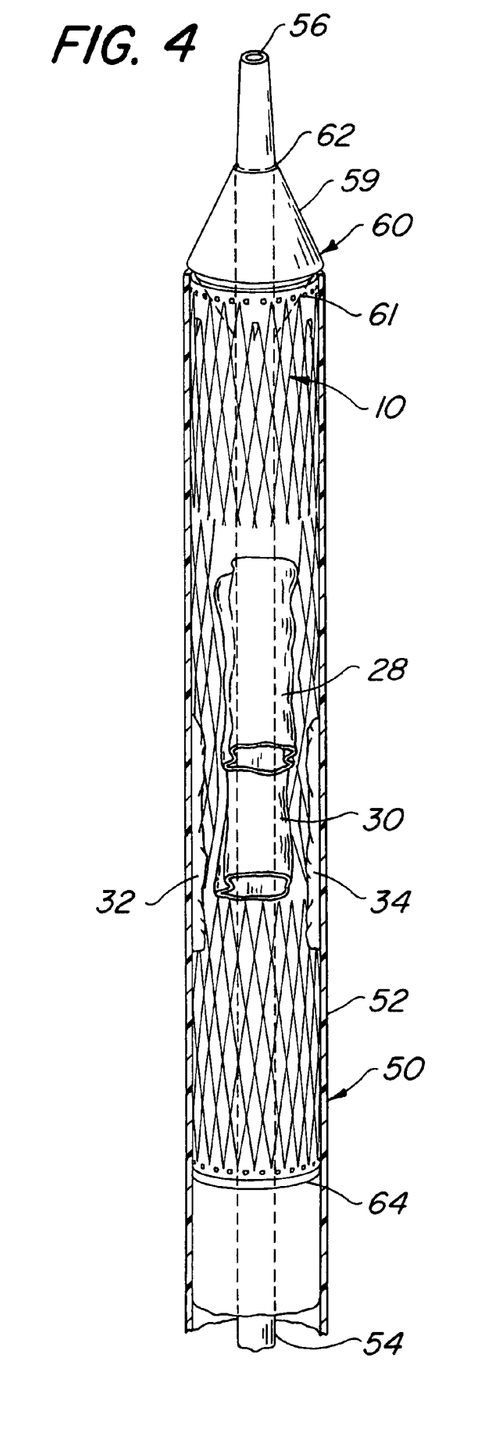
FIG. 4 is an elevation view, partially in cross section, of a broken away portion of a delivery catheter containing an endovascular prosthesis in accordance with the present invention.

FIG. 4 illustrates the distal or delivery end of catheter 50 with endovascular prosthesis 10 contained therein. Delivery catheter 50 is comprised of an outer sheath 52 and a central longitudinal tube 54 which has a hollow core 56, typically with a 0.040 inch inner diameter through which a guide wire 58 may be inserted. The central longitudinal tube 54 may be constructed of a flexible polymer or other suitable material and is provided with a flexible tip 60. Flexible tip 60 is provided with tapering both at its rostral end 59 and caudal end 61. Preferably rostral end 59 is provided with a taper which is more gradual and elongated than caudal end 61. The tip has an entrance opening 62 of the same diameter as that of the central longitudinal tube. A guide wire 58 may be threaded through central longitudinal tube 54 and opening 56, passing through tip 60. Tapered tip 60 reaches a maximal diameter which is slightly larger than outer sheath 52 so that the tip may not be pulled into outer sheath 52, but fits snugly against the outer sheath 52.

Caudal to tip 60 is a space long enough for endovascular prothesis 10, or other embodiments of endovascular prostheses, to be mounted onto the central longitudinal tube 54. Endovascular prosthesis 10 is loaded into delivery catheter 50 with central longitudinal tube 54 placed through the central lumen of endovascular prosthesis 10. Endovascular prosthesis 10, or other endovascular prosthesis, is loaded in such a way that it will have proper orientation when introduced into the patient via the chosen access artery. The chosen access artery may preferably be the femoral, carotid or axillo-brachial artery. If the prosthesis were used in other locations having branch arteries, other access locations may be chosen.

Caudal to this space for receiving endovascular prosthesis 10 or in other words caudal to endovascular prosthesis 10, a blunt thickening of the central longitudinal tube is provided which serves as a pusher rod 64. Pusher rod 64 supports the most caudal aspect of the endovascular prosthesis when mounted on the central longitudinal tube 54. Outer jacketing sheath 52 covers the length of central longitudinal tube 54, extending from the point of maximal diameter of tip 60 where it securely abuts tip 60, continuing caudally covering endovascular prosthesis 10 and the proximal aspect of pusher rod 64.

Figure 5:
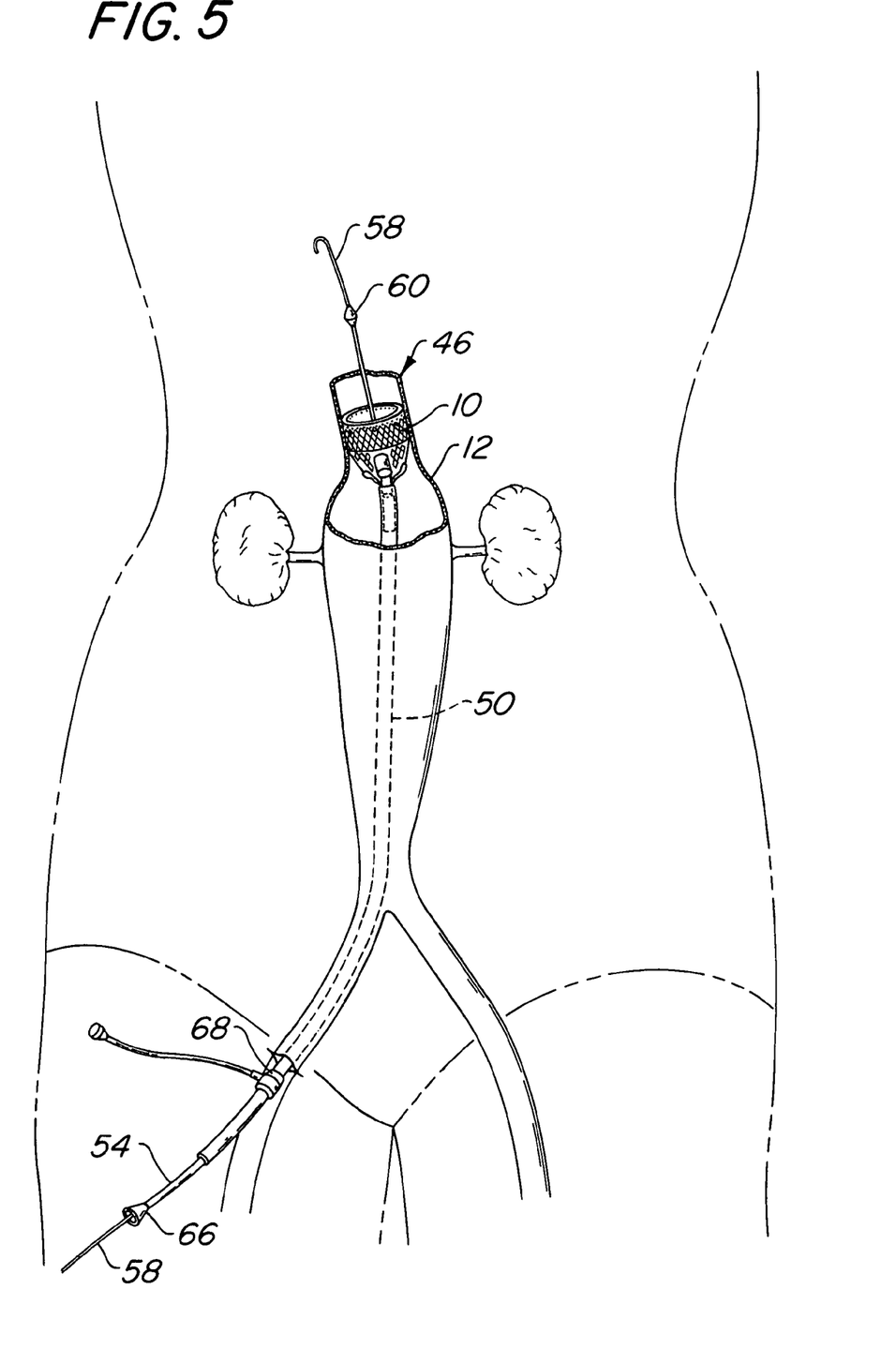
FIG. 5 is a plan view of a delivery system in the process of delivering an endovascular prosthesis in accordance with the present invention into the aorta.

As best illustrated in FIG. 5, central longitudinal tube 54 continues for a length adequate to reach the desired point for delivery of the prosthesis from the point of arterial access, such as the femoral artery as illustrated in FIG. 5. The caudal end of the delivery catheter includes an exit opening 66 through which guide wire 58 may emerge. A connector is provided for attachment of a syringe for flushing the lumen of the central longitudinal tube. The caudal end of the outer sheath has a side port with a connector 68 for a syringe to inject or irrigate the sheath's contents. The caudal end of the sheath may also have an external radial protrusion (not shown) to aid the operator's grip while retracting the sheath.

As illustrated in FIG. 5, the delivery catheter may be inserted into the body via a remote access artery, such as the femoral artery. However, other arteries may be utilized including the carotid and axillo-brachial arteries. Guide wire 58 is used to establish wire access to the region where the prosthesis is to be deployed. The delivery system is threaded onto the wire by placing the wire through the opening in the tip 60 and through the central longitudinal tube's hollow core lumen and exiting the rear of the delivery catheter 50. The delivery catheter is then advanced through the artery along the route of the wire to the desired location. Deployment of the prosthesis is accomplished by retraction of outer sheath 52 while pusher rod 64 holds endovascular prosthesis 10 in place, allowing the prosthesis to be exposed to the artery or other endograft to which it is to be attached. FIG. 5 illustrates endovascular prosthesis 10 in the process of being deployed wherein first end section 12 has been released from the delivery catheter and is expanded against the wall of the aorta 46. In a presently preferred embodiment, the supporting stents of the endovascular prosthesis are of a resilient material and automatically expand to engage the artery wall or other endovascular prosthesis. However, it is understood that the supporting stent need not be self-expanding and may be expanded by means of balloon inflation if balloon-expandable stents are employed. Other means of expanding the stent and securing the endovascular prosthesis in place may be utilized if another attachment means is chosen for the endovascular prosthesis. Stent expansion will attach the tubular first end section of endovascular prosthesis 10 securely to a native arterial wall or to a previously existing endograft, forming an impervious seal, directing blood flow through the endovascular prosthesis and its side ports. Once the stents are expanded and the prosthesis attached at the first end section, the delivery system is withdrawn from the patient.

Once endovascular prosthesis 10 is anchored in the aorta 46 as illustrated in FIG. 2, side ports 28, 30, 32 and 34 are connected to native arterial branches they are intended to supply by means of branch endografts. This is accomplished by first establishing guide wire access from a remote access artery, typically the femoral, carotid or axillo-brachial, through the prosthesis and into the desired native arterial branch. This may be facilitated by use of a guide catheter or other angiographic catheter. Once access has been established, a branch endograft of self-expanding, balloon-expandable or other design may be used to bridge the gap between the side port and the native branch artery. The distal diameter of the branch endograft is chosen to be appropriate to the diameter of the native arterial branch and a proximal diameter appropriate to that of the prosthetic side port. The branch endograft, such as branch endograft 72 for connecting between side port 32 and right renal artery 70 (shown on the left side of FIG. 2) may be placed over a guide wire and inserted into native arterial branch artery 70 (right renal artery 70) for a sufficient length so as to form an impervious seal with that branch artery when deployed. The proximal end of branch endograft 70 is similarly expanded to form an impervious seal with side port 32. In a similar manner, a guide wire is inserted sequentially into the remaining ports. For example, a guide wire may then be inserted through endovascular prosthesis 10 and side port 34 into left renal artery 76 with a branch endograft guided into position by the guide wire and expanded to form an impervious seal with both native branch artery 76 and side port 34. Although FIG. 2 illustrates the connection or communication between the side ports and the native branch arteries to be accomplished with a single branch endograft, it is understood that more than one branch endograft may be required to accomplish adequate sealing with both the native branch artery and the side port of the endovascular prosthesis. These may be done in series or sealed together in tandem. In a similar manner, branch endograft 78 may be utilized to connect to the celiac artery and branch endograft 80 may be utilized to connect to the superior mesenteric artery. The radiological markers on the side ports, such as radiological markers 36 and 38, are helpful in placement of the guide wire and placement of the branch endograft.

The second end section 14 of endovascular prothesis 10 may be anchored to disease free arterial wall or, as illustrated in FIG. 2, may be connected to another endograft 82. In this case, endograft 82 is an infrarenal endograft.

Figure 3:
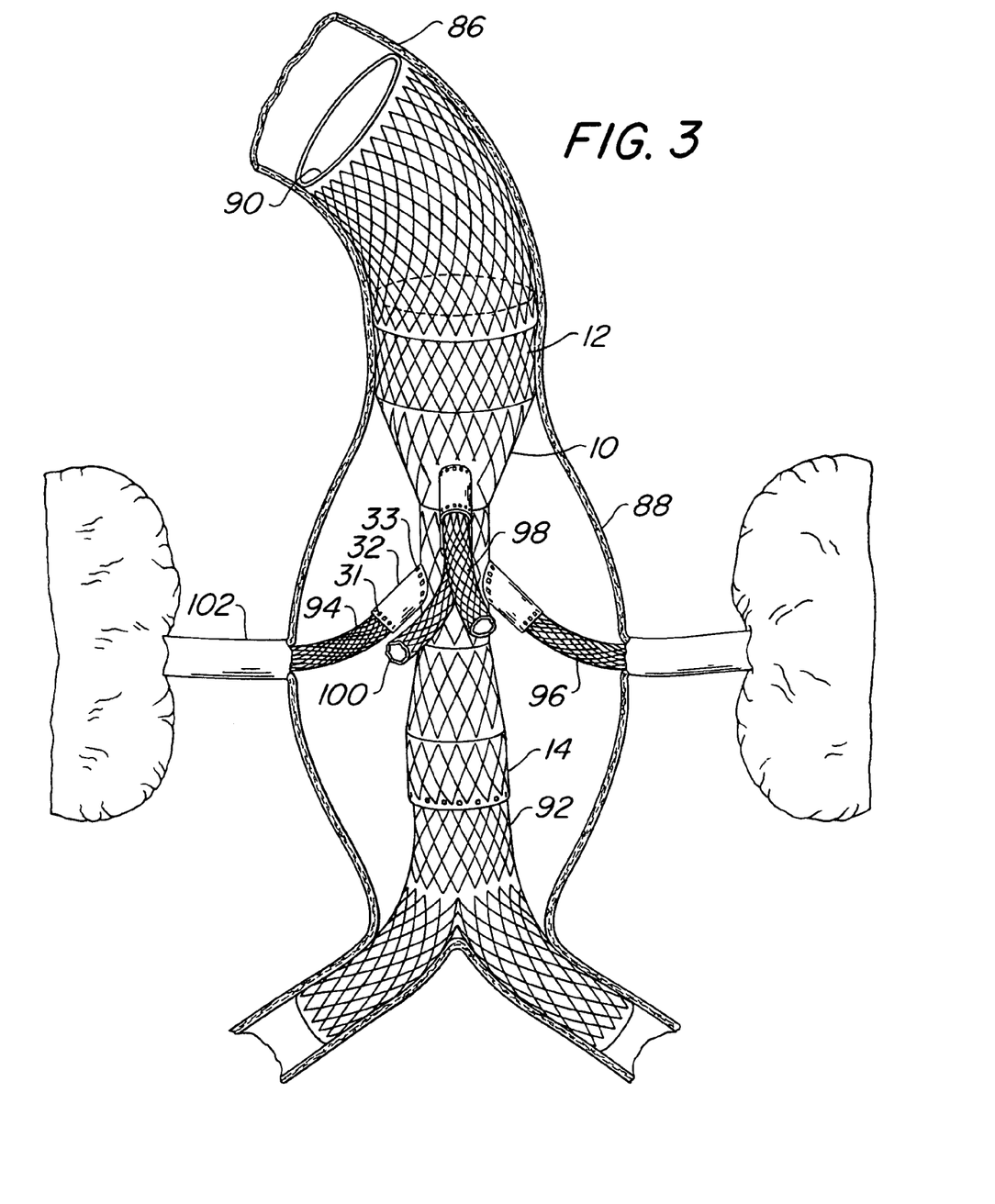
FIG. 3 is an elevation view of one embodiment of an endovascular prosthesis in accordance with the present invention implanted juxtarenally in the aorta, being attached proximally to a suprarenal endograft and being attached distally to an infrarenal endograft.

Referring now to FIG. 3, there is shown an endovascular prosthesis 10 in accordance with the present invention which has been implanted in an aorta 86 having an aneurysm 88 wherein endovascular prosthesis 10 has its first end 12 sealed within a thoracic endograft 90 and its second or distal end 14 is sealed to an infrarenal endograft 92. Thoracic endograft 90 may be preexisting or may be implanted immediately prior to the implanting of endovascular prosthesis 10. As described previously, branch endografts 94, 96, 98 and 100 would be implanted to form a bridging communication or connection between a respective side port of endovascular prosthesis 10 and the respective native branch artery. For example, branch endograft 94 would be inserted with the aid of radiologic markers 31 and 33 on renal side port 32 and sealed to side port 32 on its proximal end and sealed to native renal branch artery 102. Infrarenal endograft 92 would be sealed to the inner surface of second end section 14 of endovascular prosthesis 10.

Referring now to FIG. 6, there is shown another embodiment of an endovascular prosthesis 110 in accordance with the present invention. Similar to the embodiment illustrated in FIG. 1, endovascular prosthesis 110 is provided with a first end section 112 and a second end section 114. Endovascular prosthesis 110 is similarly provided with a midsection 120 which includes a reduced diameter central portion 122 of the midsection, a tapered section 124 extending from the first end section to the central portion of the midsection and a tapered portion 126 extending from the second end section to the central portion 122 of midsection. Endovascular prothesis 110 is similarly provided with lateral support means for substantially its entire length as described with respect to FIG. 1.

Midsection 120 is provided with side ports which are geometrically arranged approximately in the arrangement of the native branch arteries in that location. As illustrated in FIG. 6, endovascular prosthesis 110 is provided with side ports 130, 132 and 134. Side port 130 is intended to supply the innominate branch artery. Side port 132 is intended to supply the left carotid artery and side port 134 is intended to supply the left subclavian artery. Side ports 130, 132 and 134 may be provided with radiologic markers. Preferably, the side ports may be provided with rings on their distal ends to maintain patency and may also act as radiological markers.

Alternatively, rings may not be utilized and radiological markers in the form of discrete units may be formed on the side ports. Other variations of radiological markers may also be utilized in all embodiments of the endovascular prosthesis.

As illustrated in FIG. 6, endovascular prosthesis 110 may be attached to a disease free portion of the wall of the aortic arch 136 at its first end 112. Second end section 114 of endovascular prosthesis 110 may be attached and sealed to a thoracic endograft 140. Alternatively, where the portion of the aorta where second end section 114 is to be placed is not diseased, second end section 114 may be attached directly to the aortic wall.

As described previously with respect to both FIGS. 2 and 3, once endovascular prosthesis 110 is attached at its first end section 112, branch endografts may be connected and sealed to both the side port and the respective branch artery. As previously described, these are inserted using a guide wire and the stent or lateral support means of the branch endograft is expanded to form a seal at the side port and within the branch artery to the inner surface of the branch artery wall. For example, as illustrated in FIG. 6, branch endograft 142 is sealed to side port 130 and to a native branch innominate artery 144 to form a sealed fluid connection between the inner lumen of endovascular prosthesis 110 and innominate artery 144. In a similar manner, branch endograft 146 forms a sealed fluid connection between side port 132 and left carotid artery 148. In a similar manner, branch endograft 150 forms a sealed connection between side port 134 and native branch left subclavian artery 152.

Referring now to FIG. 7, there is shown another embodiment of an endovascular prosthesis in accordance with the present invention wherein the lateral support means in the form of a stent 154 is formed on the inner surface of endovascular prosthesis 156. Although it is presently preferred to have the stent or resilient stent lateral support material on the outer surface as illustrated in FIG. 1 to prevent any possibility of a guide wire catching the stent, it is within the scope of the present invention to provide the lateral support means or stent on the inner surface. Endovascular prosthesis 156 may otherwise be similar to that illustrated in FIG. 1 including a first end section and a second end section and a midsection with tapered portions.

Referring now to FIG. 8, there is illustrated another embodiment of the present invention wherein lateral support means or stent structure 164 is formed between an inner and an outer layer of impervious material so that the stent structure 164 is not exposed on endovascular prosthesis 166. Endovascular prosthesis 164 is provided with side ports 168, 170, 172 and 174. Side port 168 is located on tapered portion 176 of midsection 178. Side port 168 would be for branch endograft connection to the celiac branch artery. Side ports 170, 172 and 174 are all located on central portion 180 of midsection 178. FIG. 8 illustrates variations in the placement of the side ports on the midsection, including the tapered and central portions.

The endovascular prosthesis of the present invention may be utilized to provide an endovascular graft to bridge any diseased segment of an artery having branches. As illustrated herein, the most common applications are in the aorta, but these are illustrated merely as examples, and are not intended to be limiting. The endovascular prosthesis of the present invention may be anchored and sealed to undiseased native arterial wall or to other endografts to repair or remedy substantial segments of a diseased artery.

In the circumstance where the endovascular prosthesis of the present invention is employed to repair a segment of the abdominal aorta which involves the renal arteries but where the aorta is undiseased proximal to this location, the tubular first end of the endovascular prosthesis forms a seal with native undiseased aorta proximal to the aneurysm. In the circumstance where the prosthesis is employed to repair extensive disease of the abdominal and thoracic aorta, the thoracic aorta is first treated with a thoracic endograft, such as illustrated in FIG. 3, with proximal attachment to disease free proximal thoracic aorta and the distal extent of which terminates proximal to the origins of the visceral and renal arteries. The first end of the endovascular prosthesis of the present invention is then deployed within this previously placed thoracic endograft in a location proximal to the renal and visceral arteries as illustrated in FIG. 3. In the circumstance where the prosthesis is employed to repair a segment of the aortic arch, the tubular first end of the prosthesis forms a seal with native disease free aorta proximal to the aneurysm as illustrated in FIG. 6.

The side ports of the prosthesis are connected to native arterial branches they are intended to supply by means of branch endografts (bridging stent grafts) which span the gap as illustrated in FIGS. 2, 3 and 6. In the circumstance where the prosthesis is employed to replace the aortic arch, as in FIG. 6, the side ports would typically be employed to connect branch endografts or bridging stent grafts to the innominate, left carotid and left subclavian arteries, in each case forming an impervious seal between the bridging stent graft and the prosthesis' side port proximally and the native branch artery distally. In the circumstance where the prosthesis is employed to replace the abdominal aorta, such as in FIGS. 2 and 3, the side ports would typically be employed to connect bridging stent grafts to the celiac, superior mesenteric and renal arteries.

The second end of the endovascular prosthesis of the present invention may be used for connection to disease free native aorta or to the proximal portion of an infrarenal endograft as illustrated in FIG. 3. When the prosthesis is used for aortic arch replacement, this connection would be to a thoracic endograft as illustrated in FIG. 6, which would have its distal attachment beyond the diseased segment of aorta. When the endovascular prosthesis is used for abdominal aortic replacement, the distal connection would be to an infrarenal aortic endograft which would have distal attachment beyond the diseased segment of aorta. The appropriate endograft is intussuscepted into the tubular second end of the endovascular prosthesis of the present invention and deployed within the second end in such a way as to form an impervious seal. Alternatively, an infrarenal aortic endograft may be deployed caudally to the prosthesis and a bridging stent graft employed to connect the tubular second end of the prosthesis to the proximal portion of the infrarenal aortic endograft.

Thus all blood flow is diverted away from the diseased segment of the aorta by excluding that segment, channeling blood flow into and through the prosthesis at a location proximal to the diseased segment, distributing it to the branch arteries by means of the prosthetic side ports and branch endografts, and distributing blood flow to the distal circulation by connection of the second end to disease free aorta or another endograft.

The present invention may be embodied in other specific forms without departing from the spirit or essential attributes thereof and, accordingly, reference should be made to the appended claims, rather than to the foregoing specification as indicating the scope of the invention.

We claim:

1. An endovascular prosthesis, comprising:
a first end section having a longitudinally extending central lumen and means for laterally supporting said first end section;
a second end section having a longitudinally extending central lumen and means for laterally supporting said second end section;
a midsection formed between said first end section and said second end section and provided with a longitudinally extending central lumen in communication with said longitudinally extending central lumens of said first end section and said second end section;
said midsection having a diameter less than a diameter of said first end section and less than a diameter of said second end section;
said midsection being provided with at least one side-port adapted to be connected to a branch endograft; and
wherein said side-port has a longitudinal axis which is angled at less than 90 degrees with respect to the longitudinal direction of the central lumen of said midsection.

2. An endovascular prosthesis in accordance with claim 1 wherein said midsection includes a tapered portion extending from said first end section.

3. An endovascular prosthesis in accordance with claim 1 wherein said midsection includes a tapered portion extending from said second end section.

4. An endovascular prosthesis in accordance with claim 1 wherein said midsection is provided with a plurality of side-ports.

5. An endovascular prosthesis in accordance with claim 4 wherein said side-ports are positioned on said midsection in an arrangement approximating an arrangement of native branch vessels.

6. An endovascular prosthesis in accordance with claim 4 wherein said side-ports and their arrangement allow for accurate branch endograft placement without kinking despite variations in location of native branch vessels.

7. An endovascular prosthesis in accordance with claim 4 wherein each of said side-ports includes a proximal end attached to said midsection and a distal end and wherein each of said proximal and distal ends is provided with a radiologic marker.

8. An endovascular prosthesis in accordance with claim 7 wherein said plurality of side ports are geometrically arranged on the midsection to allow radiological identification of side ports.

9. An endovascular prosthesis in accordance with claim 4 which includes four side ports, one for the celiac artery, one for the superior mesenteric artery and two ports for the renal arteries.

10. An endovascular prosthesis in accordance with claim 9 wherein said ports for said renal arteries are arranged laterally and said port for said celiac artery is arranged centrally and positioned nearer to said first end section.

11. An endovascular prosthesis in accordance with claim 4 including three side ports arranged linearly on said midsection, one being for the innominate artery, one being for the left carotid artery and one being for the left subclavian artery.

12. An endovascular prosthesis in accordance with claim 4 wherein said plurality of side ports are each slanted in the direction of branch arteries to which they are intended to be connected.

13. An endovascular prosthesis in accordance with claim 4 wherein said plurality of side-ports are each comprised of a hollow tube having a length which is short in comparison to the distance to a native branch artery to which it is intended to be connected, said plurality of side-ports having a longitudinal axis which is slanted in the direction of branch arteries to which they are intended to be connected by branch endografts, said hollow tubular side-ports being connected to said midsection in an impervious manner, and said plurality of side-ports each being provided with radiological markers proximally and distally.

14. An endovascular prosthesis in accordance with claim 1 wherein said side-port includes a proximal end connected to said midsection and a distal end, said proximal and distal ends of said side-port being provided with radiologic markers.

15. An endovascular prosthesis in accordance with claim 1 wherein said means for laterally supporting said first end section and said second end section are stents.

16. An endovascular prosthesis in accordance with claim 15 wherein said sterns are located on an outer surface of said first and second end sections.

17. An endovascular prosthesis in accordance with claim 1 wherein said midsection is provided with lateral support means.

18. An endovascular prosthesis in accordance with claim 17 wherein said lateral support means of said first and second end sections and said midsection are located on an outer surface of said prosthesis.

19. An endovascular prosthesis in accordance with claim 17 wherein said lateral support means for said first and second end sections and said midsection are formed within a wall of said prosthesis.

20. An endovascular prosthesis in accordance with claim 1 wherein said means for laterally supporting said first end section and said second end section are resilient stents.

21. An endovascular prosthesis in accordance with claim 1 wherein said means for laterally supporting said first end section and said second end section are resilient stents which act as anchors.

22. An endovascular prosthesis in accordance with claim 21 wherein at least said first end section is provided with anchoring means in addition to said means for laterally supporting said first end section.

23. An endovascular prosthesis in accordance with claim 1
wherein the diameter of said second end section is less than the diameter of said first end section.

24. An endovascular prosthesis in accordance with claim 1 wherein said at least one side port is slanted in the direction of a branch artery to which it is intended to be connected by said branch endograft.

25. An endovascular prosthesis in accordance with claim 1 wherein said at least one side-port is comprised of a hollow tube having a length which is short in comparison to the distance to a native branch artery to which it is intended to be connected, said at least one side-port having a longitudinal axis which is slanted in the direction of a branch artery to which it is intended to be connected by said branch endograft, said hollow tubular side-port being connected to said midsection in an impervious manner, and said side-port being provided with a radiological markers proximally and distally.

26. An endovasculr prosthesis, comprising:
a first end section having a longitudinally extending central lumen and means for laterally supporting said first end section;

a second end section having a longitudinally extending central lumen and means for laterally supporting said second end section;

a midsection formed between said first end section and said second end section and provided with a longitudinally extending central lumen in communication with said longitudinally extending central lumens of said first end section and said second end section;

said midsection having a diameter less than a diameter of said first end section and less than a diameter of said second end section;

wherein said midsection includes a tapered portion extending from said first end section; and including a plurality of side ports wherein at least one side port is located on said tapered portion and at least one other side port is located on said midsection below said tapered portion.

27. An endovascular prosthetic system, comprising:

a sheath;

a central tube located within said sheath, said central tube adapted to receive a guide wire;

a pusher element within said sheath;

a tip element, including a conical forward and a conical rearward section of said tip element, a diameter of said tip element being larger than said sheath;

wherein an endovascular prosthesis may be positioned within said sheath and between said pusher and said tip for insertion into the vasculature of a body; and said endovascular prothesis including a midsection formed between two end sections, said midsection being of a smaller diameter than the diameters of said end sections and being provided with at least one side port adapted to be connected to a branch endograft.

28. A method of grafting using an endovascular prosthesis, comprising the steps of:

inserting a catheter into vasculature having at least one native branch;

releasing from said catheter an endovascular prosthesis having a midsection of reduced diameter with at least one side port formed on the midsection, said side port being provided with radiologic markers at its proximal and distal ends; and visualizing the radiologic markers on the proximal and distal ends of the side port to aid in placing a guide wire and a branch endograft for a connection between said side port and said native branch artery.

29. A method of grafting using an endovascular prosthesis in accordance with claim 28 wherein said endovascular prosthesis is provided with a resilient stent which expands said endovascular prosthesis upon release from said catheter and wherein said endovascular prosthesis is provided with a first end section and a second end section with said midsection therebetween and wherein at least one of said first end section and said second end section expands to engage an artery wall.

30. A method of grafting using an endovascular prosthesis in accordance with claim 28 wherein said endovascular prosthesis is provided with a resilient stent which expands said endovascular prosthesis upon release from said catheter and wherein said endovascular prosthesis is provided with a first end section and a second end section with said midsection therebetween and wherein at least one of said first end section and said second end section expands to engage another endovascular prosthesis.

31. A method of grafting using an endovascular prosthesis, comprising the steps of:

inserting a catheter into vasculature having a plurality of native branches;

releasing from said catheter an endovascular prosthesis having a midsection of reduced diameter with a plurality of side ports formed on the midsection, said side ports being arranged to correspond generally with the arrangement of said plurality of native branches, each of said side ports being provided with a radiologic marker at its proximal and distal ends; and visualizing the radiologic markers on the proximal and distal ends of the side ports to aid in placing guide wires and branch endografts to form a connection between the distal end of each side port and a corresponding native branch artery.

32. A method of grafting using an endovascular prosthesis in accordance with claim 31 wherein said plurality of side ports formed on the midsection fold within the length of the midsection when said endovascular prosthesis is within said catheter.

33. A method of grafting using an endovascular prosthesis in accordance with claim 31 wherein said endovascular prosthesis is provided with a resilient stent which expands said endovascular prosthesis upon release from said catheter and wherein said endovascular prosthesis is provided with a first end section and a second end section with said midsection therebetween and wherein at least one of said first end section and said second end section expands to engage an artery wall.

34. A method of grafting using an endovascular prosthesis in accordance with claim 31 wherein said endovascular prosthesis is provided with a resilient stent which expands said endovascular prosthesis upon release from said catheter and wherein said endovascular prosthesis is provided with a first end section and a second end section with said midsection therebetween and wherein at least one of said first end section and said second end section expands to engage another endovascular prosthesis.

35. An endovascular prosthesis, comprising:

a first end section having a longitudinally extending central lumen and means for laterally supporting said first end section by radial expansion;

a second end section having a longitudinally extending central lumen and means for laterally supporting said second end section by radial expansion;

a midsection formed between said first end section and said second end section and provided with a longitudinally extending central lumen in communication with said longitudinally extending central lumens of said first end section and said second end section;

said midsection having a diameter less than a diameter of said first end section and less than a diameter of said second end section when said means for laterally supporting said first end section and means for laterally supporting said second end section are not radially expanded; and said midsection being provided with at least one side-port adapted to be connected to a branch endograft; and wherein said side-port has a longitudinal axis which is angled at less than 90 degrees with respect to the longitudinal direction of the central lumen of said midsection.

36. An endovascular prosthesis in accordance with claim 35 wherein said midsection includes a tapered portion extending from said first end section.

37. An endovascular prosthesis in accordance with claim 35 wherein said midsection includes a tapered portion extending from said second end section.

38. An endovascular prosthesis in accordance with claim 35 wherein said midsection is provided with a plurality of side-ports.

39. An endovascular prosthesis in accordance with claim 38 wherein said side-ports are positioned on said midsection in an arrangement approximating an arrangement of native branch vessels.

40. An endovascular prosthesis in accordance with claim 38 wherein said side-ports and their arrangement allow for accurate branch endograft placement without kinking despite variations in location of native branch vessels.

41. An endovascular prosthesis in accordance with claim 38 wherein each of said side-ports includes a proximal end attached to said midsection and a distal end and wherein each of said proximal and distal ends is provided with a radiologic marker.

42. An endovascular prosthesis in accordance with claim 41 wherein said plurality of side ports are geometrically arranged on the midsection to allow radiological identification of side ports.

43. An endovascular prosthesis in accordance with claim 38 which includes four side ports, one for the celiac artery, one for the superior mesenteric artery and two ports for the renal arteries.

44. An endovascular prosthesis in accordance with claim 43 wherein said ports for said renal arteries are arranged laterally and said port for said celiac artery is arranged centrally and positioned nearer to said first end section.

45. An endovascular prosthesis in accordance with claim 38 including three side ports arranged linearly on said midsection, one being for the innominate artery, one being for the left carotid artery and one being for the left subclavian artery.

46. An endovascular prosthesis in accordance with claim 38 wherein said plurality of side ports are each slanted in the direction of branch arteries to which they are intended to be connected.

47. An endovascular prosthesis in accordance with claim 38 wherein said plurality of side-ports are each comprised of a hollow tube having a length which is short in comparison to the distance to a native branch artery to which it is intended to be connected, said plurality of side-ports having a longitudinal axis which is slanted in the direction of branch arteries to which they are intended to be connected by branch endografts, said hollow tubular side-ports being connected to said midsection in an impervious manner, and said plurality of side-ports each being provided with radiological markers proximally and distally.

48. An endovascular prosthesis in accordance with claim 35 wherein said side-port includes a proximal end connected to said midsection and a distal end, said proximal and distal ends of said side-port being provided with radiologic markers.

49. An endovascular prosthesis in accordance with claim 35 wherein said means for laterally supporting said first end section and said second end section are stents.

50. An endovascular prosthesis in accordance with claim 49 wherein said sterns are located on an outer surface of said first and second end sections.

51. An endovascular prosthesis in accordance with claim 35 wherein said midsection is provided with lateral support means.

52. An endovascular prosthesis in accordance with claim 51 wherein said lateral support means of said first and second end sections and said midsection are located on an outer surface of said prosthesis.

53. An endovascular prosthesis in accordance with claim 51 wherein said lateral support means for said first and second end sections and said midsection are formed within a wall of said prosthesis.

54. An endovascular prosthesis in accordance with claim 35 wherein said means for laterally supporting said first end section and said second end section are resilient stents.

55. An endovascular prosthesis in accordance with claim 35 wherein said means for laterally supporting said first end section and said second end section are resilient stents which act as anchors.

56. An endovascular prosthesis in accordance with claim 55 wherein at least said first end section is provided with anchoring means in addition to said means for laterally supporting said first end section.

57. An endovascular prosthesis in accordance with claim 35 wherein the diameter of said second end section is less than the diameter of said first end section.

58. An endovascular prosthesis in accordance with claim 35 wherein said at least one side port is slanted in the direction of a branch artery to which it is intended to be connected by said branch endograft.

59. An endovascular prosthesis in accordance with claim 35 wherein said at least one side port is comprised of a hollow tube having a length which is short in comparison to the distance to a native branch artery to which it is intended to be connected, said at least one side port having a longitudinal axis which is slanted in the direction of a branch artery to which it is intended to be connected by said branch endograft, said hollow tubular side-port being connected to said midsection in an impervious manner, and said side-port being provided with a radiological markers proximally and distally.

60. An endovascular prosthesis, comprising:
  a first end section having a longitudinally extending central lumen and means for laterally supporting said first end section by radial expansion;
  a second end section having a longitudinally extending central lumen and means for laterally supporting said second end section by radial expansion;
  a midsection formed between said first end section and said second end section and provided with a longitudinally extending central lumen in communication with said longitudinally extending central lumens of said first end section and said second end section;
  said midsection having a diameter less than a diameter of said first end section and less than a diameter of said second end section when said means for laterally supporting said first end section and means for laterally supporting said second end section are not radially expanded;
  wherein said midsection includes a tapered portion extending from said first end section; and
  including a plurality of side ports wherein at least one side port is located on said tapered portion and at least one other side port is located on said midsection below said tapered portion.

* * * * *